United States Patent [19]

Marciel

[11] Patent Number: Plant 7,520

[45] Date of Patent: May 14, 1991

[54] ROSE PLANT NAMED DEVNOVIA

[75] Inventor: Stanley G. Marciel, Aptos, Calif.

[73] Assignee: DeVor Nurseries, Inc., Watsonville, Calif.

[21] Appl. No.: 383,615

[22] Filed: Jul. 24, 1989

[51] Int. Cl.[5] ..... A01H 5/00

[52] U.S. Cl. ..... Plt./19

[58] Field of Search ..... Plt. 18, 19, 20

*Primary Examiner*—Howard J. Locker

*Attorney, Agent, or Firm*—Charles W. Rummler

[57] ABSTRACT

A new and distinct greenhouse rose plant particularly distinguished by its continuous and profuse production of relatively small flowers of a magenta rose coloration from early Spring to Winter under greenhouse culture, the flowers being borne singly on strong, upright stems of medium length on a vigorous, upright plant having abundant foliage.

1 Drawing Sheet

BACKGROUND OF THE NEW PLANT

This new rose variety originated as a seedling of a hybrid produced by me at Pleasanton, Calif. by my crossing the rose variety DeVite (U.S. Plant Pat. No. 5,172) with the pollen of the variety Independence '76 (U.S. Plant Pat. No. 3,902), this particular seedling having been selected for propagation because of the very pleasing, generally magenta coloration of its relatively small flowers which are borne singly on strong stems of medium length having good foliage and I propagated that seedling by budding at Pleasanton, Calif. with such satisfactory results that I continued the propagation in that manner through several successive generations and thereby determined that its novel characteristics would hold true from generation to generation and appeared to be firmly fixed.

DESCRIPTION OF THE DRAWING

My new rose plant is illustrated by the accompanying photographic drawing which shows a face view of a fully opened bloom together with a sweetheart bud of medium size together with a newly opening flower of about ¼ of its fully opened size, the colors shown being as nearly true to those herein specified as is reasonably possible to obtain by conventional photographic procedures.

DESCRIPTION OF THE NEW VARIETY

The following is a detailed description of my new rose plant based upon observation of plants grown in greenhouse at Pleasanton, Calif., with the color designations being according to The R.H.S. Color Chart published by The Royal Horticultural Society of London, England.

THE PLANT

Origin: Seedling.

Parentage:

*Seed parent.*—The variety DeVite (U.S. Plant Pat. No. 5,172).

*Pollen parent.*—The variety Indpendence '76 (U.S. Plant Pat. No. 3,902).

Classification:

*Botanic.*—Greenhouse Rose.

Form: An upright free branching bush of medium height.

Growth habit: Vigorous and sturdy.

Flowering stem:

*Length.*—Averaging about 38 to 60 cm.

*Color.*—Yellow green, 144B.

Foliage:

*Quantity.*—Moderately abundant.

*Number of leaves.*—7, from last flower cut, averaging about 115 mm. long and of odd-pinnate shape.

Leaflets:

*Size.*—Terminally, about 61 mm. long and about 44 mm. wide.

*Shape.*—Generally elliptic with acute apex and crenate margins.

*Lateral leaflets.*—Two or four in number with size averaging about 48 mm. long and 35 mm. wide.

*Texture.*—Leathery.

*Aspect.*—Smooth and glossy.

*Color of leaflets.*—Upper side — Yellow green, 147A. Under side — 147B.

Ribs and veins: Prominent and grooved on upper side of leaf and rounded on underside of leaf.

Rachis:

*Length.*—About 25 mm. for leaf with 3 leaflets and about 40 mm. for leaf with 5 leaflets.

Petioles:

*Length.*—About 10 to 14 mm.

Thorns:

*Number.*—Average.

*Size.*—About 7 mm. long.

*Color.*—Greyed red, 178A with yellow green, 147B on tips.

THE BUD

Size: Medium sweetheart.

*Diameter.*—About 30 to 34 mm.

*Depth.*—About 33 mm.

Shape: Urn-shaped.

Rate of openings: Slow.

Color of petals:

*When sepals first divide.*—Spiraea red, 63B.

*When petals begin to unfurl.*—Magenta rose, 64D.

Sepals:

*Number.*—Five.

*Shape.*—Elliptic with acuminate apex.

*Character.*—The sepals stand up when the flowers open.

*Color.*—Inside — Yellow green, 147D. Outside — Green, 143C.

Calyx:
*Shape.*—Funnel-shaped.
*Size.*—Medium, broad and long.
*Splitting.*—Calyx does not split.
*Aspect.*—Smooth.
Peduncle of flower stem:
*Length.*—About 90 mm.
*Character.*—Erect, slender and smooth.
*Color.*—Yellow green, 144B.

THE FLOWER

Blooming habit: Continuous and profusely from early Spring to Winter blooming freely under glass until Winter.
Size of bloom: Small.
*Diameter.*—About 43 to 50 mm.
*Depth.*—About 35 mm.
Borne: Singly.
Shape: Cup-shaped when bloom first opens and when bloom matures becoming uniformly imbricated at full bloom.
Petalage:
*Number.*—About 16.
*Arrangement.*—Imbricated.
*Form.*—Oboviate with cuspidate tip and ruffled margins.
*Texture.*—Leathery.
*Appearance.*—Velvety.
*Color.*—Outer petals: Upper side: Body — Magenta rose, 64D with base of yellow, 3D. Reverse side: Body — Spiraea red, 63C with base of yellow green, 150D. Inside petals: Upper side: Body — Spiraea red, 63C with base of yellow, 5C. Reverse side: Body — 63C with base of yellow green, 154D.
Petaloids:
*Number.*—1 to 6.
*Size.*—About 13 mm.
*Color.*—Spiraea red, 63C with base of yellow, 5C.
Peduncle of flower stem:
*Length.*—About 9 cm.
*Color.*—Yellow green, 144B.
*Character.*—Sturdy and upright.

Fragrance: Light.
Persistance: The petals stay on the stem for about 21 days.
Discoloration after full bloom: Slight.
Disease resistance: Moderately resistant to mildew, rust, and black spot as observed at Pleasanton, Calif.
Lasting quality: Long-lasting both on the plant and as a cut flower.

THE REPRODUCTIVE ORGANS

Stamens:
*Number.*—About 1 to 5.
*Arrangement.*—Introse.
*Anthers.*—Size: About 2 mm. Color: Yellow orange, 20A.
*Filaments.*—Length: About 5 mm. Color: Yellow green, 154C.
*Pollen.*—Color: Yellow orange, 20A.
Pistils:
*Number.*—About 76. *Styles.*—Length: About 7 to 10 mm. Color: Yellow green, 154D.
*Stigmas.*—Color: Chrome yellow, 14D.
Character of the ovaries: Long, slender with covering of silvery hairs.
Fertility: This variety is fertile. The hips are globular shaped but depressed at top, color at maturity is Yellow Orange, 22 A.

This new variety is a magenta sweetheart which produces abundant blooms most nearly resembles Uropa (unpatented), but is distinguished by having a much brighter color and the stems are more sturdy and longer.

The seed parent is a white intermediate and the pollen parent is a light red intermediate.

I claim:

1. The new and distinct rose variety, substantially as herein shown and described, characterized by its profuse and continuous production of generally magenta colored flowers of generally small size and by its vigorous upright and free branching growth habit as a greenhouse rose.

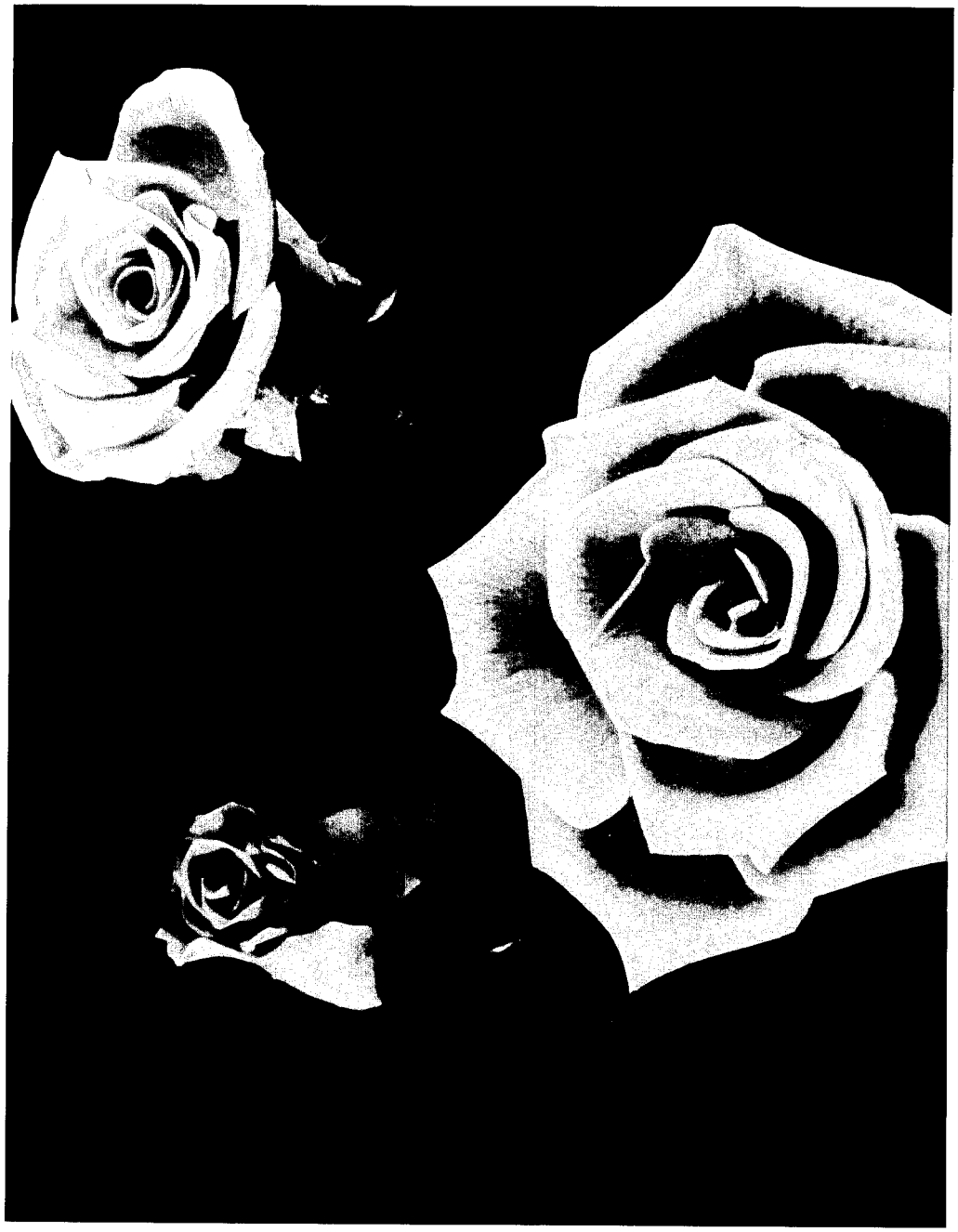

* * * * *